US008888714B1

(12) United States Patent
Soto (10) Patent No.: US 8,888,714 B1
(45) Date of Patent: Nov. 18, 2014

(54) AUTOMATIC BLOOD DRAW SYSTEM AND METHOD

(71) Applicant: Richard Soto, West Hollywood, CA (US)

(72) Inventor: Richard Soto, West Hollywood, CA (US)

(*) Notice: Subject to any disclaimer, the term of this patent is extended or adjusted under 35 U.S.C. 154(b) by 0 days.

(21) Appl. No.: 14/158,270

(22) Filed: Jan. 17, 2014

Related U.S. Application Data (60) Provisional application No. 61/880,301, filed on Sep. 20, 2013.

(51) Int. Cl.
A61B 5/00 (2006.01)
A61B 5/153 (2006.01)
A61B 5/15 (2006.01)

(52) U.S. Cl.
CPC ......... *A61B 5/1535* (2013.01); *A61B 5/150748* (2013.01)
USPC .......................................... 600/576; 600/573

(58) Field of Classification Search
CPC . A61B 5/1405; A61B 5/1438; A61B 5/15003
USPC ................................................ 600/573, 576
See application file for complete search history.

(56) References Cited

U.S. PATENT DOCUMENTS

| 5,629,498 | A | * | 5/1997 | Pollock et al. ............... 177/15 |
| 2002/0035341 | A1 | * | 3/2002 | Rohrscheib et al. ......... 600/573 |
| 2004/0127815 | A1 | * | 7/2004 | Marchitto et al. ............ 600/573 |
| 2008/0045818 | A1 | * | 2/2008 | Wood et al. .................. 600/310 |
| 2008/0161723 | A1 | * | 7/2008 | Keenan et al. ............... 600/573 |
| 2008/0195043 | A1 | * | 8/2008 | Schwach et al. ............. 604/116 |
| 2009/0287115 | A1 | * | 11/2009 | Abbott ......................... 600/576 |
| 2010/0168535 | A1 | * | 7/2010 | Robinson et al. ............ 600/309 |
| 2010/0274202 | A1 | * | 10/2010 | Hyde et al. ................... 604/272 |
| 2011/0082711 | A1 | * | 4/2011 | Poeze et al. ...................... 705/3 |
| 2011/0288405 | A1 | * | 11/2011 | Razavi et al. ................ 600/424 |
| 2012/0190981 | A1 | * | 7/2012 | Harris et al. ................. 600/439 |

* cited by examiner

*Primary Examiner* — Sean Dougherty
*Assistant Examiner* — Daniel Cerioni
(74) *Attorney, Agent, or Firm* — ARC IP Law, PC; Joseph J. Mayo (57) ABSTRACT

Enables cleaning a user's target area around a vein, starting an intravenous catheter placement into a user's vein, drawing blood from a vein, transferring the blood into one or more test tubes and labeling the test tubes. Includes a housing configured to enable a user to fit their arm into the apparatus, a blood pressure cuff, a scanner, a computer system, one or more needles, test tubes and labels. The scanner may scan the user's arm for target veins. Uses an antiseptic solution or antiseptic pads to wipe down a target area, such that a selected needle of appropriate size is lowered and inserted into the targeted vein to draw blood. Embodiments may lower and fill the test tube with the user's drawn blood, label the test tubes with the user's information and dispose the needle into a biohazard removable container.

20 Claims, 4 Drawing Sheets

AUTOMATIC BLOOD DRAW SYSTEM AND METHOD

This application is claims the benefit of U.S. Provisional Patent Application Ser. No. 61/880,301, filed 20 Sep. 2013, the specification of which is hereby incorporated herein by reference.

BACKGROUND OF THE INVENTION

1. Field of the Invention

One or more embodiments of the invention are related to using a needle to draw blood from a user's arm for testing or donating purposes. More particularly, but not by way of limitation, one or more embodiments of the invention enable an automatic blood draw system and method that enables starting an intravenous catheter placement into a user's vein, drawing blood from a vein, cleaning a user's target area around the vein, transferring the drawn blood into one or more respective test tubes and labeling the test tubes.

2. Description of the Related Art

Current solutions for drawing blood from a patient or donor are manual in nature and generally require a person who has developed the skill to select an appropriate vein for needle puncture in order to draw blood. For example, a technician may place a tourniquet around the upper part of the arm to apply pressure to the whole lower part of the arm causing the veins to rise and engorged with blood. The technician may then wipe the area where the vein is, surface clean the area with alcohol, and insert the needle into the vein. Once the test tube is filled with blood the technician may hand label the test tube with the user information.

Generally, current blood drawing techniques present various problems. For example, one problem occurs when a technician punctures the skin but misses the particular target vein. The technician then removes the needle and starts over again.

Another problem with typical blood drawing techniques occurs when the technician misses the particular targeted vein and has to adjust the needle in order to advance the needle to the targeted vein, which may cause bruising and/or damage to the vein. In this scenario the patients experience multiple needle punctures until the targeted vein is located.

In addition, another problem with typical blood drawing techniques sometimes occurs when technicians remove a needle from a user's arm and then accidentally puncture themselves. This puts the technician's own life at risk from blood borne pathogen contamination. Furthermore, using current typical blood drawing techniques, the technician may insert the needle into the targeted vein too deep, thus puncturing the other end wall of the targeted vein, which may cause blood leakage under the skin, which results in a condition known as a hematoma.

Generally, using current methods, the technician may also mistakenly puncture the surface of the skin, a nerve and/or an artery of the user, instead of the targeted vein, causing damage and pain to the user's arm. In doing so, for example, the damage and pain from the punctured nerve may last for weeks or even months until the nerve has healed. Also, for example, if the technician mistakenly punctures an artery followed by removal of the needle from the artery, without proper pressure applied to the immediate vicinity of the punctured artery, the user may bleed to death.

Furthermore, using typical blood drawing techniques as known in the art, the technician may mislabel test tubes being used with incorrect user information, leading to various errors during distribution, testing and diagnosis.

For at least the limitations described above there is a need for an automatic blood draw system.

BRIEF SUMMARY OF THE INVENTION

One or more embodiments described in the specification are related to automatic blood drawing systems and methods that enable one or more of automatic blood drawing, blood infusion and medication infusion. The blood drawing system is configured enable a user to fit their arm into the apparatus. A user, for example, may include a patient and/or a donor. In at least one embodiment of the invention, the system and method include an automatic blood drawing system having a housing that may include a blood pressure cuff, a scanner, for example an ultrasound scanner, a computer system, one or more needles, one or more test tubes and one or more labels. In one or more embodiments, the computer system may enter the user's information into the automatic blood drawing system, and the blood pressure cuff may wrap around the user's arm and place pressure on a user's arm. As such, for example, the blood pressure cuff may fasten around the user's upper arm, place pressure on the user's lower arm and engorge the user's veins with blood. The scanner, in at least on embodiment, may scan the user's arm for one or more user veins. Specifically, one or more embodiments of the automatic blood draw system may select a vein by scanning the entire arm to select the largest vein, and may then insert the needle directly into the vein to draw blood. In at least one embodiment of the invention, once the test tubes are full of blood, the automatic blood draw system may label the test tubes with the user's name and other appropriate user information.

In addition, embodiments may include one or more needles of varying sizes that may be inserted into a vein of the one or more veins of the user, and one or more test tubes such that the one or more needles may draw blood from the user and transfer the drawn blood into the one or more test tubes respectively. Furthermore, embodiments may include one or more labels for the one or more test tubes that may be placed on the one or more test tubes respectively with the user's information. In one or more embodiments, the computer system may enter the user's information into the automatic blood drawing system, prior to the blood drawing procedure, manually and/or automatically.

As stated, in at least one or more embodiments of the invention, once the user's information is entered into the computer system, the scanner may scan said user's entire arm for a largest vein for venipuncture. In addition to, or alternatively, embodiments of the invention may include one or more intravenous catheters, within the housing, that may infuse one or more of blood and medications to the user. In one or more embodiments of the invention, the computer system may select a needle from the one or more needles, of varying sizes, of an appropriate size in order to accommodate the user's scanned largest vein, and/or select an intravenous catheter from the one or more intravenous catheters that may be inserted into the user's scanned largest vein. The one or more needles, for example, may vary in size from 24 gauges to 14 gauges. However, as one of ordinary skill would appreciate, other sizes for the one or more needles are within the scope of art of the invention.

By way of one or more embodiments of the invention, the system may include a bracket, within the housing, such that once the largest vein of the user has been selected, the computer system may lower the bracket onto a target area on the user's arm to place pressure on the user's arm and hold the user's largest vein in place within the target area. In addition, in at least one embodiment, the housing may include an antiseptic solution and/or one or more antiseptic pads, such that the computer system may secrete the antiseptic solution and/or one or more antiseptic pads onto the target area to wipe and clean the target area on the user's arm. In one or more embodiments, once the user's largest vein has been scanned and selected, the system has an option of setting up the machine to draw blood using the one or more needles, and/or select to start an intravenous line using the one or more intravenous catheters for infusing fluids and/or medication. According to one or more embodiments, once the one or more options have been selected, and the appropriately sized needle and/or intravenous catheter have been selected, the system may enable the computer system to insert one or more of the selected needle of appropriate size and/or the selected intravenous catheter into the user's largest vein, for successful vein puncture. In addition, using the computer system, embodiments may one or more of enable the selected needle to draw blood from the user's largest vein and transfer the drawn blood into a respective test tube of the one or more test tubes, and enable the selected intravenous catheter to infuse one or more of blood and medications to the user. In at least one embodiment, the one or more test tubes include test tubes of different colors and different sizes respectively associated with one or more different tests being administered. As such, embodiments of the invention enable the system to appropriately select one or more test tubes of different colors and different sizes to transfer the user's blood into, depending on the test being administered to the user, and the amount of blood required to be drawn. As such, an external user such as a physician, nurse, or any other healthcare practitioner may easily locate each test tube and easily assign each test tube to a specific user for a specific blood test, once the procedure is complete.

By way of one or more embodiments of the invention, once a specific amount of test tubes of the one or more test tubes have been filled with the user's blood, embodiments may enable the computer system to automatically label each of the respective test tubes with the one or more labels with the user's information. Embodiments of the invention may include gauze, within the housing, such that the system may remove the one or more needles and intravenous catheters from the user's vein, lower the gauze onto the target area, and place pressure on the target area. For example, in one or more embodiments, the gauze may be a 2×2 sized gauze, although as one of ordinary skill in the art would appreciate, other sized gauzes may be used as appropriate within the scope of art of the invention. In addition, for example, pressure may be placed on the target area for about 3 minutes, although it is noted as one of ordinary skill in the art would appreciate, pressure may be placed for more or less than 3 minutes, depending on a respective situation unique to the user.

In at least one or more embodiments of the invention, the housing includes a paper tape, such that after the respective time of pressure being placed on the user's arm, using the computer system, the system may place the paper tape onto the gauze, in order to secure a bandage on the user's target area. For example, the paper tape may be a 1-inch piece of paper tape, however as one of ordinary skill in the art would appreciate, other appropriate sized paper tapes may be used.

By way of one or more embodiments, the housing may include a removable biohazard container, such that the system, via the computer system, may dispose one or more of the selected needle and the selected intravenous catheter into the biohazard container. As such, the removable biohazard container may be emptied by the external user, once the removable biohazard container is full. In at least one embodiment of the invention, the computer system may generate an alert to the external user, indicating that the removable biohazard container is full and needs to be emptied. In one or more embodiments of the invention, the alert may be one or more of a visual alert, a sound alert, a text alert, a vibratory alert, or any combination thereof, provided one or more of a screen and light-emitting diode (LED) located on a surface of the housing.

Embodiments of the invention provide a system and method that enables drawing blood from a user's vein and starting an intravenous catheter placement by puncturing a user's skin once, which eliminates any risk of human error of not locating the best, and or largest, targeted vein to draw blood from, and eliminates the possibility of using multiple needles, or multiple punctures, to accurately draw blood from a user, and/or infuse the user with blood and/or medication.

In addition, embodiments of the invention provide a system and method of protecting healthcare workers, such as nurses, physicians and/or other healthcare providers, from mistakenly receiving an accidental needle prick during a blood draw and/or intravenous catheter line placement. Furthermore, using embodiments of the invention herein, greatly reduces any errors of test tube mislabeling by providing a quick, automatic and easy method of appropriately labeling each test tube with respective user information using the automatic blood draw system.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

A system and method of automatically drawing blood will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

One or more embodiments described in the specification are related to automatic blood drawing systems and methods that enable one or more of automatic blood drawing, blood infusion and medication infusion. The blood drawing system is configured to enable a user to fit the user's arm into the apparatus. A user, for example, may include a patient and/or a donor.

Figure 1:
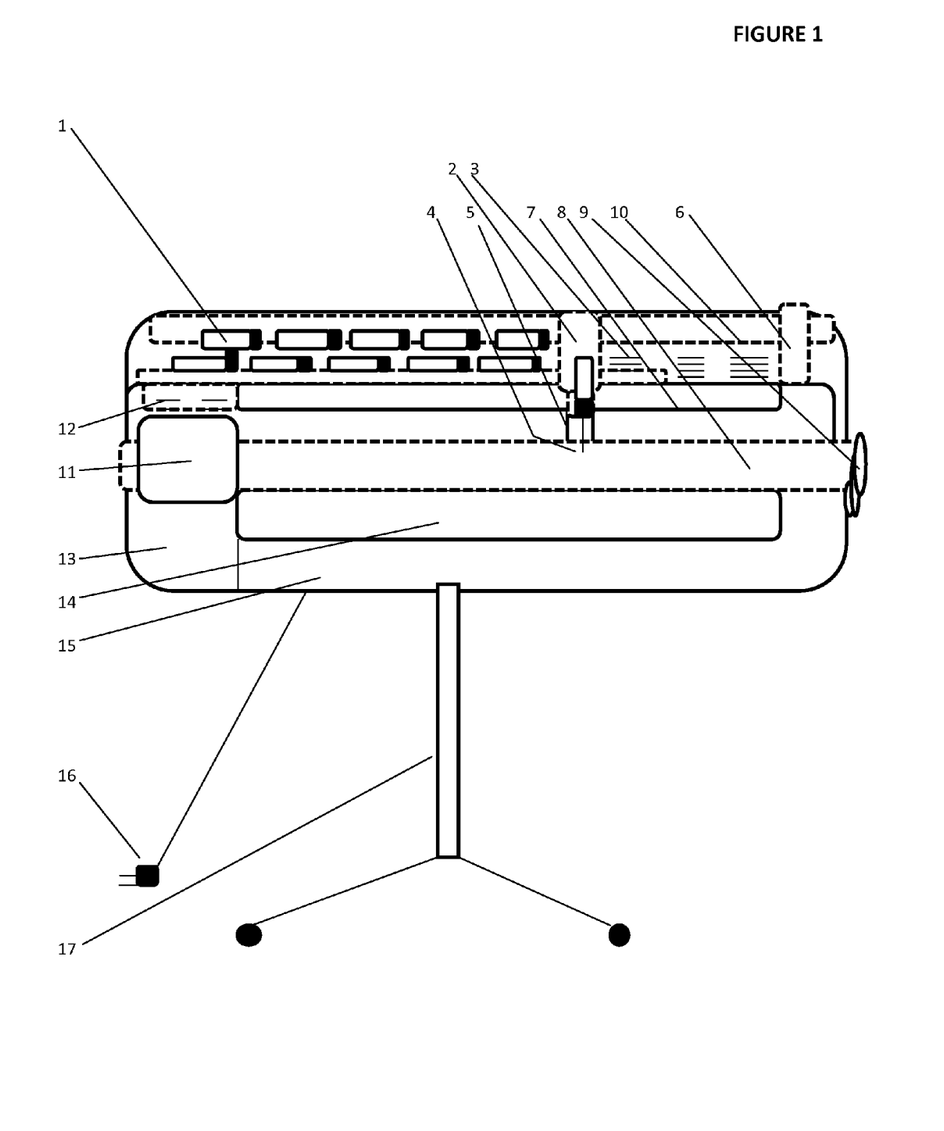
FIG. 1 illustrates a side view of an embodiment of the automatic blood draw system.

FIG. 1 illustrates a side view of an embodiment of the automatic blood draw system. As shown, the automatic blood draw system includes a housing with one or more test tubes 1, a test tube chamber 2 enabling, for example, the one or more test tubes 1 to be lowered into test tube chamber 2, either mechanically or by pressure and/or gravity, one or more antiseptic pads and/or solution 3 and a needle 4. A plurality of needles may be included and held in needles storage chamber 12, for example 24 gauge to 14 gauge needles or needles of any other size. In at least one embodiment of the invention, the system may include a blood pressure cuff 11, an upper scanner 7 for example that is implemented in one or more embodiments with an ultrasound scanner or any other type of scanner that is capable of detecting a vein, a lower scanner 14 that may also be an ultrasound scanner or any other type of scanner that is capable of detecting a vein, a computer system and storage chamber for the computer system 15 that may identify the user's one or more veins using the ultrasound transducer and receiver in the upper and lower scanner, memory 20, one or more intravenous catheters 22, paper tape 23, a removable biohazard container 24, and one or more labels 21. In at least one embodiment of the invention, the labels 21 may include adhesive labels that are stored along with the one or more test tubes 1 in labeled test tubes storage chamber 10. See also FIG. 3 for a close-up view of the needle and sensor arrangement.

According to one or more embodiments of the system, the computer system may instruct one or more of elements within the housing as detailed herein. For example, the computer system may accept and enter the user's information into the automatic blood drawing system, for example into memory 20 associated with the computer held in the storage area. The computer may further control the blood pressure cuff 11 to wrap around the user's arm, when the user's arm is placed in area 8 and the user's fingers are placed in area 9, wherein the cuff is controlled by the computer to place pressure on the user's arm. As such, for example, the blood pressure cuff 11 may fasten around the user's upper arm, place pressure on the user's lower arm and engorge the user's veins with blood. The scanner, including the upper scanner 7 and the lower scanner 14, in at least on embodiment, may scan the user's arm for one or more user veins. In at least one embodiment of the invention, the computer system may include a computer program that may identify the veins, and select the largest vein using one or more algorithms to measure the diameter of each detected by in width and in length. Any known algorithm or imaging for scanners including optical tomography or ultrasound may be utilized as one skilled in the art will appreciate so long as it is capable of detecting a vein, location and size thereof. The advantages on non-ionizing radiation systems enable scanning without harmful radiation, however any type of scanner may be utilized including X-ray scanners in other embodiments.

In addition, embodiments may include the one or more needles 4 of varying sizes that may be inserted into a vein of the one or more veins of the user, such that the one or more needles 4 may draw blood from the user and transfer the drawn blood into the one or more test tubes 1 respectively. In at least one embodiment, the one or more selected test tubes 1 may be lowered and collected via the needle 4 by suction. Furthermore, in at least one embodiment, the one or more labels 21 for the one or more test tubes 1 may be placed on the one or more test tubes respectively 1 with the user's information, in a test tube and label storage area, as discussed regarding FIG. 2 below. According to at least one embodiment, the user's information may include one or more of the user's name, date of birth, address, identification number, test type being administered, or any combination thereof. In one or more embodiments, the computer system may enter the user's information into the automatic blood drawing system, prior to the blood drawing procedure, manually and/or automatically.

In at least one or more embodiments of the invention, once the user's information is entered into the computer system, one or both of the scanners 7, 14 may scan said user's arm (310 in FIG. 3) for a largest vein (311 in FIG. 3) for venipuncture. In addition to, or alternatively, embodiments of the invention may include one or more intravenous catheters 22, within the housing, that may infuse one or more of blood and medications to the user. In one or more embodiments of the invention, the computer system may select a needle from the one or more needles 4, of varying sizes, of an appropriate size in order to accommodate the user's scanned largest vein as identified by the computer system, and/or select an intravenous catheter from the one or more intravenous catheters 22 that may be inserted into the user's scanned largest vein as identified by the computer system. The one or more needles 4, for example, may vary in size from 24 gauges to 14 gauges or any other size as desired. In one or more embodiments, the computer system may then select a vein, from the one or more detected and identified veins, using a correct measure of the diameter in width and in length, and select the appropriate sized needle, from the varying sizes, therefrom. However, as one of ordinary skill would appreciate, other sizes for the one or more needles are within the scope of art of the invention. In one or more embodiments, as the needle and associated test tube are lowered into the arm of the user, the scanner detects the depth at which the tip of the needle is at and adjusts the depth to enter the vein and may move up or down during the process to keep the need within the vein. In one or more embodiments, the angle at which the need enters the user's arm is not 90 degrees as shown in the figure for ease of understanding of one embodiment of the invention, but rather may be at 5, 10, 15 degrees or any other angle to enable an angled entry into the vein.

By way of one or more embodiments of the invention, as shown in FIG. 1, the system may include a bracket 5, within the housing, such that once the largest vein of the user has been selected and identified by the computer system, the computer system may lower the bracket 5 onto a target area on the user's arm to place pressure on the user's arm and hold the user's largest vein in place within the target area. In one or more embodiments of the invention, the bracket 5 may include a square bracket, however, as one ordinary skill in the art will appreciate, any other shaped bracket may be appropriate within the scope of the invention that may lowered and placed onto the target area to place pressure around the entire target area on the user's arm. In addition, in at least one embodiment, the housing may include the antiseptic solution and/or one or more antiseptic pads 3, such that the computer system may instruct the system to secrete the antiseptic solution and/or one or more antiseptic pads 3 onto the target area to wipe and clean the target area, such as a square target area when using the square bracket 5, on the user's arm. In one or more embodiments, once the user's largest vein has been scanned and selected, the system has an option of setting up the machine to draw blood using the one or more needles 4, and/or select to start an intravenous line using the one or more intravenous catheters 22 for infusing fluids and/or medication. According to one or more embodiments, once the one or more options have been selected, and the appropriately sized needle 4 and/or intravenous catheter 22 have been selected, the system may enable the computer system to insert one or more of the selected needle 4 of appropriate size and/or the selected intravenous catheter 22 into the user's largest vein, for successful vein puncture. In addition, using the computer system, embodiments may one or more of enable the selected needle to draw blood from the user's largest vein and transfer the drawn blood into a respective test tube of the one or more test tubes 1, and enable the selected intravenous catheter 22 to infuse one or more of blood and medications to the user. In at least one embodiment, the one or more test tubes 1 include test tubes of different colors and different sizes respectively associated with one or more different tests being administered. As such, embodiments of the invention enable the system to appropriately select one or more test tubes 1 of different colors and different sizes to transfer the user's blood into, depending on the test being administered to the user, and the amount of blood required to be drawn. As such, an external user such as a physician, nurse, or any other healthcare practitioner may easily locate each test tube and easily assign and store each test tube to a specific user for a specific blood test, once the procedure is complete. Embodiments of the invention may utilize any known technique for moving test tubes within the apparatus, and any known technique for coupling needles to the test tubes including a mechanical or electromagnetic actuator that holds a needle and test tube and moves the needle and test tube together until they are coupled. Embodiments may also utilize any technique of moving the coupled needle and test tube to any angle desired for moving to and away from the vein, including for example any type of robotic arm or assembly that one skilled in the art will recognize.

By way of one or more embodiments of the invention, once a specific amount of test tubes of the one or more test tubes 1 have been filled with the user's blood, embodiments may enable the computer system to automatically label each of the respective test tubes 1 with the one or more labels 21 with the user's information. Embodiments of the invention may include a gauze and gauze storage chamber 6, within the housing, such that the system may remove the one or more needles 4 and/or the intravenous catheters 22 from the user's vein, lower the gauze 6 onto the target area, and place pressure on the target area to stop any bleeding from the user's punctured vein. For example, in one or more embodiments, the gauze 6 may be a 2×2 sized gauze, although as one of ordinary skill in the art would appreciate, other sized gauzes may be used as appropriate within the scope of art of the invention. In addition, for example, pressure may be placed on the target area for about 3 minutes, although it is noted as one of ordinary skill in the art would appreciate, pressure may be placed for more or less than 3 minutes, depending on a respective situation unique to the user.

In at least one or more embodiments of the invention, the housing includes a paper tape 23, such that after the respective time of pressure being placed on the user's arm, using the computer system, the system may place the paper tape 23 onto the gauze 6 on the user's arm, in order to secure a bandage on the user's target area to stop by bleeding from the user's punctured vein. For example, the paper tape 23 may be a 1-inch piece of paper tape, however as one of ordinary skill in the art would appreciate, other appropriate sized paper tapes may be used. By way of one or more embodiments, the housing may include a removable biohazard container 24, such that the system, via the computer system, may dispose one or more of the selected needle 4 and the selected intravenous catheter 22 into the biohazard container 24. As such, the external user may empty the removable biohazard container 24 once the removable biohazard container 24 is full. In at least one embodiment of the invention, the system housing may include a computer interface touch screen and chamber thereof 13, enabling the external user to enter the user's information manually, if needed. Furthermore, in one or more embodiments, the computer interface touch screen 13 may depict text, output sound, output light, and output a vibration or any combination thereof, using the touch screen. Optionally, the computer interface touch screen may include one or more light-emitting diodes (LEDs), of one color or various colors. As such, for example, in at least one embodiment of the invention, the computer system may generate an alert to the external user, via the computer interface touch screen 13, such as indicating that the removable biohazard container 24 is full and needs to be emptied. Other alerts may include indicating to the external user medical data regarding the user such as blood pressure information, any sudden changes in blood pressure, and alerting the external user of any other data related to the user. In one or more embodiments of the invention, the alert may be one or more of a visual alert, a sound alert, a text alert, a vibratory alert, or any combination thereof, provided by one or more of the tough screen and one or more of the light-emitting diodes (LEDs), that may be located on a surface housing of the computer interface touch screen.

In at least one embodiment of the invention, the automatic blood drawing system may include a power plug 16 for accessing electrical power from an external source, internal one or more batteries (not shown) and a detachable and optional stand 17. For example, embodiments of the invention enable the system to operate with or without the power plug 16, such as by using the internal batteries. As such, if the external source of power, for any reason, cannot provide power to the system, the system will continue to operate without disconnecting, interrupting or terminating any parts of the procedure. In addition, according to at least one embodiment of the invention, the machine may be stationary and/or mobile, in order to move the machine from one location to another and from one user to another easily. According to one or more embodiments of the invention, the detachable and optional stand 17 may include, wheels and a height adjustment element, in order to easily rotate the machine, move the machine, and shift the machine up and down to accommodate to different user locations and placements.

Figure 2:
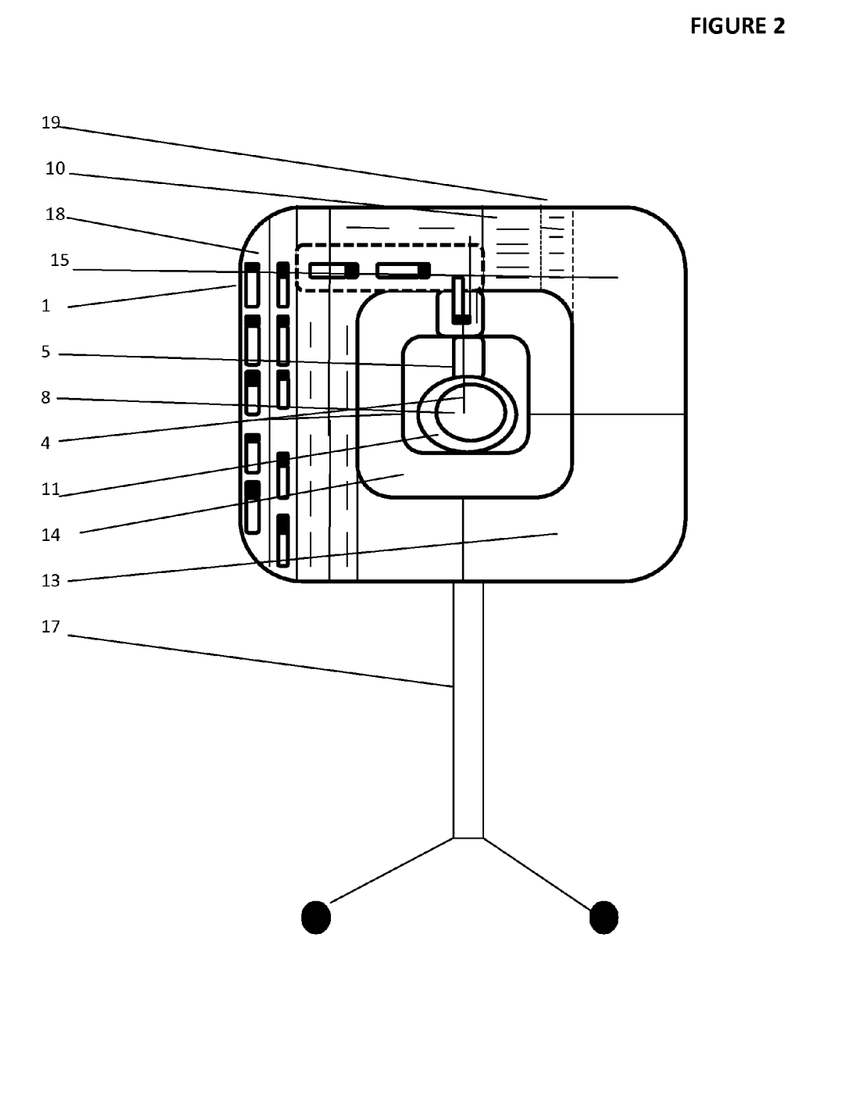
FIG. 2 illustrates a sectional side view of an embodiment of the automatic blood draw system.

FIG. 2 illustrates a sectional side view of the automatic blood draw machine and system according to one or more embodiments of the invention. As shown in FIG. 2, the sectional side view illustrates the one or more test tubes 1, the storage chamber for the one or more labels 10, the storage chamber for the computer system 15, the bracket 5, for example a square bracket, the area for inserting the user's arm 8, the one or more needles 4, the blood pressure cuff 11, the lower scanner 14, the computer and interface touch screen and chamber 13, the detachable and optional stand 17 and the power plug 16 for accessing electrical power from an external source. Although embodiments described herein may include two computers, as one skilled in the art will recognize, one computer may be utilized to control any or all components within the system and provide an interface for a user to instruct the apparatus to perform any function described herein.

In addition, as shown in FIG. 2, one or more embodiments of the invention may include a test tube storage chamber 18 for storing the one or more test tubes prior to the procedure and an antiseptic solution and/or one or more antiseptic pads storage chamber 19 for the antiseptic solution and/or one or more antiseptic pads 3.

Figure 3:
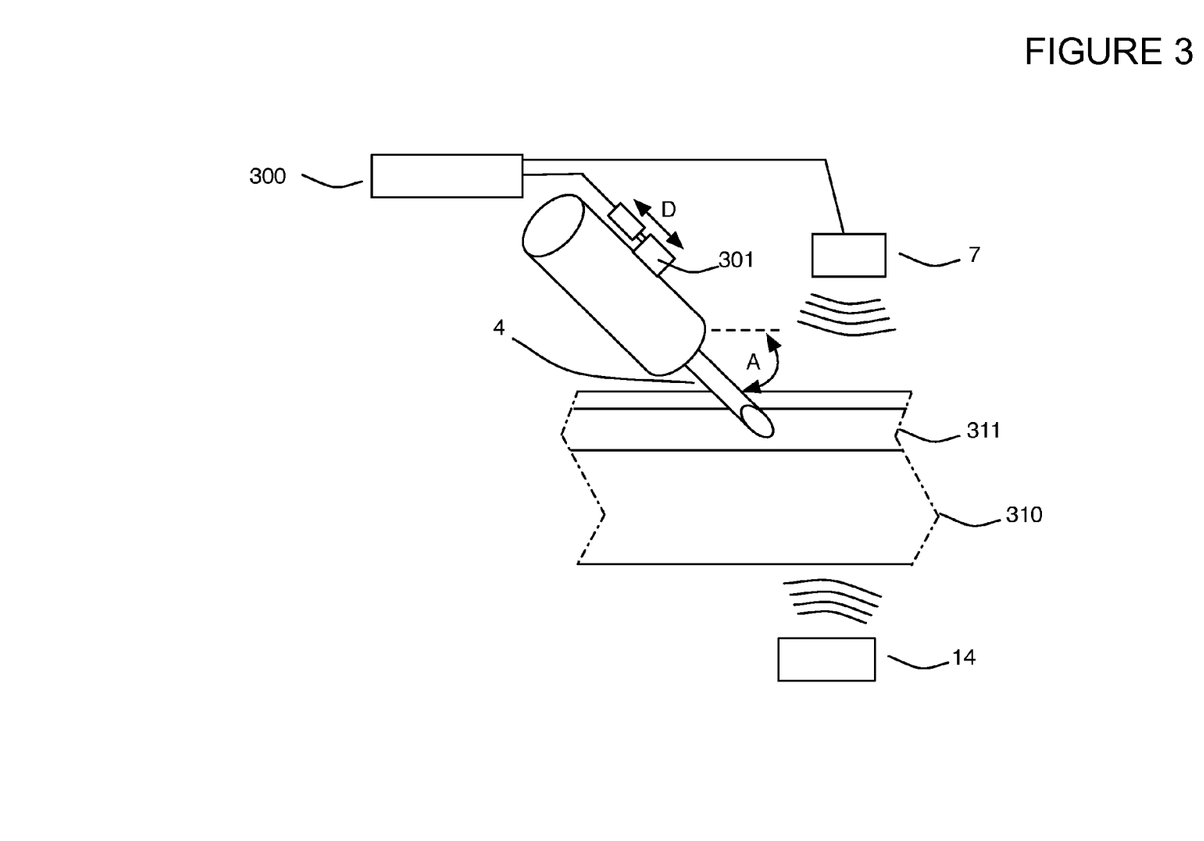
FIG. 3 illustrates a close-up view of the needle and sensor operatively coupled to enable precise depth positioning of the needle in a user's arm.
Figure 4:
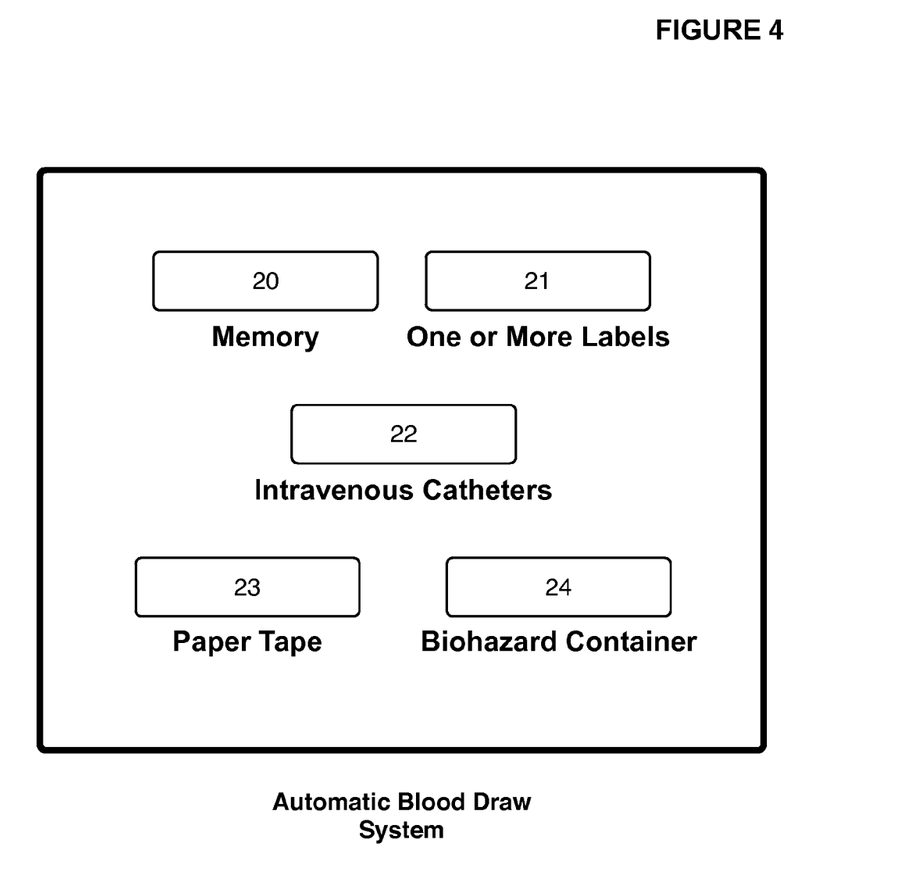
FIG. 4 illustrates a side view of the automatic blood draw system with a memory, one or more labels, intravenous catheters, paper tape and a biohazard container according to at least one embodiment of the invention.

FIG. 3 illustrates a close-up view of the needle and sensor operatively coupled to enable precise depth positioning of the needle in a user's arm. As shown, computer 300, which may be any computer previously described, for example as housed in computer system storage chamber 15 is coupled with physical actuator 301 to set a distance D based on sensor values obtained from upper sensor 7 and/or optional lower sensor 14. Computer 300 for example may control sensors 7 and/or optional sensor 14 to output and receive ultrasound or optical or electromagnetic signals or any other type of signals that may be utilized to determine an upper and lower position of the walls of vein 311, for example the largest vein in user's arm 310. In one or more embodiments, a smaller vein may be selected if desired or as instructed by an attending physician or nurse via inputs accepted by computer 300. As distance D is increased, the sensor values of sensor 7 and/or optional sensor 14 detect the depth of needle 4 within vein 311 and adjust distance D so that the tip of needle 4 is between the upper and lower wall of vein 311. In one or more embodiments, the distance D may increase in order to puncture the vein and then decrease for example after puncture to position the tip of needle 4 midway or in any other spatial orientation between the upper and lower walls of vein 311. Optional sensor may be coupled with computer 300 as well, but this is not shown for brevity and ease of illustration. In one or more embodiments physical actuator 301 may be coupled to the bracket or any other structure within the apparatus and may hold the test tube in any known manner so long as the actuator is capable of moving the tip of the needle in and out of a vein in the user's arm 310. For example, in one embodiment if the signal received from sensor 7 shows that the tip of needle 4 is 1 mm within vein 311 and 2 mm above the lower wall of vein 311, then the distance D may be increased 0.5 mm divided by sin(angle A) of entry to obtain an actual depth increase of 0.5 mm. The entry angle A may be pre-configured to any desired angle and/or may be set by altering the relationship between the apparatus and physical actuator 301 to set angle A for example. In this scenario if the entry angle is set to 10 degrees, then a 0.5 mm depth increase vertically into the vein requires 0.5 mm/sin (10 degrees) or 0.174 which equals 2.87 mm of distance D increase.

While the invention herein disclosed has been described by means of specific embodiments and applications thereof, numerous modifications and variations could be made thereto by those skilled in the art without departing from the scope of the invention set forth in the claims.

What is claimed is:

1. An automatic blood drawing system comprising:
    a housing comprising
        a computer system coupled with a blood pressure cuff, scanner, memory, one needle or a plurality of needles of varying sizes, at least one actuator for the one needle or the plurality of needles of varying sizes, one or more test tubes, and one or more labels, wherein said computer system is configured to
        accept a user's information into said memory; and,
        wrap the blood pressure cuff around a user's arm and place pressure on the user's arm after the user's information has been accepted into said memory;
        scan said user's arm to locate and select one or more veins of the user using the scanner after wrapping the blood pressure cuff around a user's arm and placing pressure on the user's arm;
        obtain an entry angle A to insert the needle, the entry angle being based on the vein selected during the scan of the user's arm;
        determine a distance D to move a tip of the needle to obtain a vertical depth of the needle in the selected vein and above a lower wall of the selected vein as D=vertical depth/sin(A), after said obtain said entry angle A;
        inserting the tip of the needle from the one needle or from the plurality of needles of varying sizes at an angle equal to the entry angle A into said selected vein of said one or more veins of the user at by moving the tip of the needle by distance D to locate the needle in the vein selected during the scan of the user's arm and above the lower wall of the vein selected during the scan of the user's arm after determining the distance D, wherein the inserting of the tip of the needle draws blood from said user into said one or more test tubes respectively; and,
        place one or more labels on said one or more test tubes respectively with said user's information after the tip of the needle has been inserted and after said one or more test tubes are filled with said user's blood.

2. The automatic blood drawing system of claim 1, wherein said computer system is further configured to enter said user's information into said automatic blood drawing system prior to said one needle or said plurality of needles drawing blood from said user.

3. The automatic blood drawing system of claim 1, wherein said scanner is further configured to scan said user's arm for a largest vein and wherein said computer system is further configured to identify the largest vein.

4. The automatic blood drawing system of claim 3, further comprising one or more intravenous catheters, within the housing, configured to infuse one or more of blood and medications to said user, using said computer system.

5. The automatic blood drawing system of claim 4, wherein said computer system is further configured to one or more of
    select a needle from said one needle or said plurality of needles of varying size of an appropriate size configured to accommodate said user's largest vein, and
    select an intravenous catheter from said one or more intravenous catheters configured to be inserted into said user's largest vein.

6. The automatic blood drawing system of claim 5, further comprising a bracket, within the housing, wherein said computer system is further configured to lower said bracket onto a target area on said user's arm to place pressure on said user's arm and hold said user's largest vein in place within said target area.

7. The automatic blood drawing system of claim 6, further comprising an antiseptic solution and/or one or more antiseptic pads, within the housing, wherein said computer system is further configured to secrete said antiseptic solution onto said target area to clean said target area on said user's arm.

8. The automatic blood drawing system of claim 7, wherein said computer system is further configured to
    insert one or more of said selected needle of appropriate size and said selected intravenous catheter into said user's largest vein; and
    one or more of enable said selected needle to draw blood from said user's largest vein and transfer said drawn blood into a respective test tube of said one or more test tubes, and enable said selected intravenous catheter to infuse one or more of blood and medications to said user.

9. The automatic blood drawing system of claim 8, wherein said computer system is further configured to label said respective test tube with said one or more labels with said user's information.

10. The automatic blood drawing system of claim 9, further comprising a gauze, within said housing, wherein said computer system is further configured to remove one or more of said selected needle and said selected intravenous catheter from said user's largest vein, lower said gauze onto said target area, and place pressure on said target area.

11. The automatic blood drawing system of claim 10, further comprising paper tape, within said housing, wherein said computer system is further configured to place said paper tape onto said gauze.

12. The automatic blood drawing system of claim 11, further comprising a biohazard container, within said housing, wherein said computer system is further configured to dispose one or more of said selected needle and said selected intravenous catheter into said biohazard container.

13. An automatic blood drawing method comprising:
coupling a computer system with a blood pressure cuff, scanner, memory, one needle or a plurality of needles of varying sizes, at least one actuator for the one needle or the plurality of needles of varying sizes, one or more test tubes, and one or more labels;
accepting a user's information into said memory of said computer system;
wrapping the blood pressure cuff around said user's arm and placing pressure on the user's arm after accepting said user's information into memory;
scanning said user's arm to locate and select one or more veins of the user using the scanner after wrapping the blood pressure cuff around a users arm and placing pressure on the user's arms;
obtaining an entry angle A to insert the needle, the entry angle being based on the vein selected during the scan of the user's arm;
determining a distance D to move a tip of the needle to obtain a vertical depth of the needle in the selected vein and above a lower wall of the selected vein as D=vertical depth/sin(A), after obtaining said entry angle A;
inserting the tip of the needle from the one needle or from the plurality of needles of varying sizes at an angle equal to the entry angle A into said selected vein of said one or more veins of the user at by moving the tip of the needle by distance D to locate the needle in the vein selected during the scan of the user's arm and above the lower wall of the vein selected during the scan of the user's arm after determining the distance D, wherein the inserting of the tip of the needle draws blood from said user into said one or more test tubes respectively; and,
placing one or more labels on said one or more test tubes respectively with said user's information after the tip of the needle has been inserted and after said one or more test tubes are filled with said user's blood.

14. The automatic blood drawing method of claim 13, further comprising scanning said user's arm for a largest vein using said scanner, and identifying the largest vein using said computer system.

15. The automatic blood drawing method of claim 14, further comprising one or more of
selecting a needle from said one needle or said plurality of needles of varying size with an appropriate size configured to accommodate said user's largest vein using said computer system, and
selecting an intravenous catheter from one or more intravenous catheters and pushing said selected intravenous catheter into said user's largest vein.

16. The automatic blood drawing method of claim 15, further comprising lowering a bracket from within said housing onto a target area on said user's arm, using said computer system, to place pressure on said user's arm and hold said user's largest vein in place within said target area.

17. The automatic blood drawing method of claim 16, further comprising secreting one or more of an antiseptic solution and one or more antiseptic pads from within said housing onto said target area to clean said target area on said user's arm, using said computer system;
inserting one or more of said selected needle of appropriate size and said selected intravenous catheter into said user's largest vein, using said computer system; and
one or more of enabling said selected needle to draw blood from said user's largest vein and transferring said drawn blood into a respective test tube of said one or more test tubes using said computer system, and enabling said selected intravenous catheter to infuse one or more of blood and medications to said user, using said computer system.

18. The automatic blood drawing method of claim 17, further comprising labeling said respective test tube with said one or more labels, from within said housing, with said user's information using said computer system.

19. The automatic blood drawing method of claim 18, further comprising
removing one or more of said selected needle and said selected intravenous catheter from said user's largest vein, using said computer system,
lowering a gauze from within said housing to said target area, using said computer system,
placing pressure on said target area, using said computer system, and
placing a paper tape onto said gauze, using said computer system.

20. The automatic blood drawing method of claim 19, further comprising disposing one or more of said selected needle and said selected intravenous catheter into a biohazard container, using said computer system, wherein said biohazard container is within said housing.

* * * * *